United States Patent
Rhee et al.

(10) Patent No.: US 8,337,865 B2
(45) Date of Patent: Dec. 25, 2012

(54) MODIFIED FLAGELLIN IMPROVED TOLL-LIKE RECEPTOR 5 STIMULATING ACTIVITY

(75) Inventors: Joon Haeng Rhee, Gwangju (KR); Shee Eun Lee, Gwangju (KR); Soo Young Kim, Hwasun-gun (KR)

(73) Assignee: Industry Foundation of Chonnam National University, Gwangju (KR)

( * ) Notice: Subject to any disclaimer, the term of this patent is extended or adjusted under 35 U.S.C. 154(b) by 0 days.

(21) Appl. No.: 13/333,857

(22) Filed: Dec. 21, 2011

(65) Prior Publication Data

US 2012/0201855 A1    Aug. 9, 2012

Related U.S. Application Data

(62) Division of application No. 12/526,187, filed as application No. PCT/KR2008/000709 on Feb. 5, 2008, now Pat. No. 8,236,327.

(30) Foreign Application Priority Data

Feb. 9, 2007  (KR) .............................. 2007-0013846
Feb. 4, 2008  (KR) .............................. 2008-0011330

(51) Int. Cl.
*A61K 39/106*    (2006.01)
(52) U.S. Cl. ................... 424/261.1; 424/191.1; 530/350

(58) Field of Classification Search .................. None
See application file for complete search history.

(56) References Cited

FOREIGN PATENT DOCUMENTS

| WO | WO 2005070455 A1 | 8/2005 |
|---|---|---|
| WO | WO 2006078657 A2 | 7/2006 |

OTHER PUBLICATIONS

Amrisha Verma et al., Roles of Specific Amino Acids in the N Terminus of *Pseudomonas aeruginosa* Flagellin and of Flagellin Glycosylation in the Innate Immune Response, 2005.
Chinese Patent Office, Chinese Office Action issued in corresponding CN Application No.200880004041.0, dated Aug. 3, 2011.
Chothia et al (The EMBO Journal, 1986, 4/5:823-26).
European Patent Office Search Report corresponding to Supplementary European Search Report for EP 08 71 2360 (inventor:Rhee et al.) dated Mar. 11, 2010.
Mikayama et al. (Nov. 1993. Proc. Natl. Acad. Sci. USE, vol. 90:10056-10060).
Rudinger et al. (Jun. 1976, Peptide Hormones. Biol. Council. pp. 5-7).

*Primary Examiner* — Jennifer Graser
(74) *Attorney, Agent, or Firm* — Sughrue Mion, PLLC

(57) ABSTRACT

Disclosed herein are flagellin mutants having an enhanced activity of stimulating the toll-like receptor-5 (hereinafter referred to as "TLR5"). More specifically, disclosed are flagellin mutants, prepared by point-mutating some of the amino acids of a TRL5 agonist flagellin so as to enhance the TRL-stimulating activity of the flagellin.

5 Claims, 5 Drawing Sheets

FIG. 1

| Salmonella FliC | | | | V. vulnificus FlaB | | | |
|---|---|---|---|---|---|---|---|
| Upper subunit | | Lower subunit | | Upper subunit | | Lower subunit | |
| A. A. | Type of A. A. | A. A. | Type of A. A. | A. A. | Type of A. A. | A. A. | Type of A. A. |
| D70 | Acidic | N101 | Polar | D70A | Acidic | N101 | Polar |
| N133 | Polar | D108 | Acidic | N135D | Polar | E108 | Acidic |
| A150 | Non-P | R93 | Basic | A151 | Non-P | R93 | Basic |
| D152 | Acidic | Q410 | Polar | N153 | Polar | V292 | Non-P |

A : Denaturing gel analysis
B : Native gel analysis

1. Size marker
2. FlaB (Wild type)
3. FlaB (D70A)
4. FlaB (R93A)
5. FlaB (L97W)
6. FlaB (N101A)
7. FlaB (S103W)
8. FlaB (E108A)
9. FlaB (N135D)
10. FlaB (A151W)
11. FlaB (N153W)
12. FlaB (V291W)

A : Denaturing gel analysis
B : Native gel analysis

1. Size marker
2. FlaB (Wild type)
3. FlaB (D70A)
4. FlaB (N135D)
5. FlaB (D70A/N135D)

MODIFIED FLAGELLIN IMPROVED
TOLL-LIKE RECEPTOR 5 STIMULATING
ACTIVITY

This application is a Divisional of U.S. patent application Ser. No. 12/526,187, filed Aug. 6, 2009, issued as U.S. Pat. No. 8,236,327, which is a National Stage application of PCT/KR2008/000709, filed Feb. 5, 2008, which claims priority from Korean patent Application No. 10-2007-0013846, filed Feb. 9, 2007, and from Korean patent Application No. 10-2008-0011330, filed Feb. 4, 2008 in the Korean Intellectual Property Office, the disclosures of which are incorporated herein in their entirety by reference.

SEQUENCE LISTING

The instant application contains a Sequence Listing which has been submitted in ASCII format via EFS-Web and is hereby incorporated by reference in its entirety. Said ASCII copy, created on Feb. 15, 2012, is named Q114416.txt and is 71,196 bytes in size.

TECHNICAL FIELD

The present invention relates to flagellin mutants having an enhanced activity o/f stimulating the toll-like receptor-5 (hereinafter referred to as "TLR5"), and more particularly to flagellin mutants, prepared by point-mutating some of the amino acids of a TRL5 agonist flagellin so as to enhance the TRL5-stimulating activity of the flagellin.

BACKGROUND ART

Flagella are important structural elements determining the motility of bacteria and are generally composed of a hook, a basal body and a filament. It is known that flagella contribute to the swimming or swarming motility, the taxis of bacteria, the adhesion of pathogenic microorganisms to host cells, and formation of biofilms. A subunit protein forming the flagellar filament is referred as flagellin, and flagellins are regularly assembled to form the filament. Hayashi et al. reported that TLR5 expressed on mammalian cells recognize the flagellin of gram-negative and gram-positive bacteria to activate NF-κB (Hayashi F, Smith K D, Ozinsky A, Hawn T R, Yi E C, Goodlett D R, Eng J K, Akira S, Underhill D M, Aderem A: Nature 410:1099-1103, 2001).

Toll-like receptors (TLRs) are typical "Pattern Recognition Receptors (PRRs)", which recognize "Pathogen Associated Molecular Patterns (PAMPs)" present in pathogens and are found not only in mammals, but also on the surfaces of insects and plant cells. Thirteen kinds of TLRs have been found to date, and studies on agonists of TLRs have been actively conducted (Akira S, Uematsu S, Takeuchi O: Cell 124 (4): 783-801, 2006).

PRRs such as TLRs are distributed on the surface or in the cytoplasm of host cells, induce innate immune responses after being stimulate with various PAMPs, and furthermore, regulate adaptive immune responses. Thus, TLR agonists can serve targets suitable for the development of various immune regulators, particularly vaccine adjuvants.

As used herein, the term "vaccine adjuvants" refers to substances which can enhance, prolong or accelerate Ag-specific immune responses induced by vaccine antigens, when they are co-administered with vaccines. Vaccine adjuvants approved for use in the human body include aluminum phosphate, aluminum hydroxide, and squalene emulsion. Vaccine adjuvants must satisfy at least one of the following five requirements: 1) regulation of expression of co-stimulatory molecules on the surface of antigen-presenting cells, induction of antigen-specific T-lymphocyte responses, or immunomodulation such as the modulation of cytokine secretion; 2) antigen presentation; 3) induction of CD8+ cytotoxic T lymphocyte responses; 4) targeting; and 5) depot generation.

Ideal vaccine adjuvants: 1) must be safe; 2) must be biodegraded in vivo; 3) must show potent protective or therapeutic immune responses compared to when antigens are administered alone; 4) must be chemically or biologically verified substances; 5) preferably act at concentrations lower than antigens; and 6) must have a long half life, such that they can be readily applied commercially or clinically.

Substances, which are currently used as vaccine adjuvants or considered for use as vaccine adjuvants, include: 1) mineral salts such as aluminum hydroxide gel; 2) surfactant substances; 3) bacteria-derived substances; 4) cytokines or hormones; 5) polyanions; 6) polyacryl; 7) carriers; 8) living vectors comprising virus; and 9) vehicles, such as mineral oil liposomes. Among them, protein-derived vaccine adjuvants, which are currently actively studied and receive great attention, include *Vibrio cholerae*-derived cholera toxin (CT) and *Escherichia coli*-derived heat-labile toxin (LT). It was reported that these vaccine adjuvants induce the production of antigen-specific antibodies in mucosal areas and sera and induce the expression of B7-2 on the surface of antigen-presenting cells (APCs) to stimulate the co-stimulatory signaling of CD4+ helper T cells. However, these adjuvants are exotoxins having high enterotoxicity, and thus studies focused on reducing the toxicity thereof and increasing the adjuvanticity thereof, are in progress.

As disclosed in PCT International Patent Publication No. WO 2005/070455, the present inventors constructed a transposon mutant library in order to screen adhesion and invasion factors of *Vibrio vulnificus*, and analyzed the Tn-flanking regions in three clones, which lost their adhesion to host cells and their motility, and, as a result, the present inventors identified two flagella operons consisting of 56 genes. In this analysis process, it was found that *V. vulnificus* has a total of six flagellin genes (flaA, flaB, flaF, flaC, flaD and flaE), and among them, the flaB gene is the major component of the flagellins. The present inventors studied the possibility that the flagellin recombinant protein (FlaB), the component of the polar flagellin of *V. vulnificus*, can be applied as a component vaccine against *V. vulnificus*, and, as a result, the present inventors found that the flagellin recombinant protein (FlaB), besides high antigenicity, also has a strong vaccine adjuvant effect. To elucidate this finding, the present inventors conducted further studies. As a result, it was demonstrated that, when a vaccine antigen tetanus toxoid was administered to the nasal cavity of test animals together with flagellin, the flagellin amplified the effect of the vaccine by transmitting a signal to the TLR5 of host cells to activate the immune system, and when a lethal dose of tetanus toxin was challenged to mice immunized by administering tetanus toxoid and flagellin, the flagellin induced complete defense immunity to the toxin, suggesting that the flagellin had an excellent mucosal vaccine adjuvant effect (Lee S E, Kim S Y, Jeong B C, Kim Y R, Bae S J, Ahn O S, Lee J J, Song H C, Kim J M, Choy H E, Chung S S, Kweon M N, Rhee J H.: Infect. Immun. 74: 694-702, 2006).

Among various TLR agonists, flagellin stimulating TLR5 is a protein component, unlike other TLR agonists [CpG-DNA, MLP (mycoplasmal lipopeptide)]. Thus, it is possible to synthesize recombinant flagellin proteins, the quality of which can be continuously controlled, and in addition, it is possible to construct various recombinant fusion proteins having an enhanced activity of stimulating TLR5.

According to the results of studies on the three-dimensional structure of flagellin, polar amino acid residues and charged amino acid residues in a flagellin monomer react with those in another monomer, so that the axial interaction between the monomers occurs to form a polymer, thus forming the characteristic filament structure of flagellin (Yonekura K, Maki-Yonekura S, Namba K: Complete atomic model of the bacterial flagellar filament by electron cryomicroscopy. Nature. 2003 424(6949):643-50; Samatey F A, Imada K, Nagashima S, Vonderviszt F, Kumasaka T, Yamamoto M, Namba K: Structure of the bacterial flagellar protofilament and implications for a switch for supercoiling. Nature. 2001 410(6826):331-7). According to the study of Smith et al., it was reported that TLR5 does not recognize a filament-type flagellin polymer, but recognizes flagellin monomers (Smith K D, Andersen-Nissen E, Hayashi F, Strobe K, Bergman M A, Barrett S L, Cookson B T, Aderem A. Toll-like receptor 5 recognizes a conserved site on flagellin required for protofilament formation and bacterial motility. Nat. Immunol. 2003 4(12):1247-53).

A common problem, observed in preventive and therapeutic vaccines (vaccines for infectious diseases, autoimmune diseases, allergic diseases and cancers), which are currently used in clinical applications, is that these vaccines lack effective vaccine adjuvants, which can specifically amplify relevant responses. Thus, there is a strong need to develop safer and more effective vaccine adjuvants.

DISCLOSURE

Technical Problem

Accordingly, the present inventor have prepared recombinant flagellin mutants, which can suppress polar-charge reactions that are involved in the axial interaction between flagellin monomers, of the flagellin gene flaB of *V. vulnificus*, by changing amino acid residues anticipated to be involved in the axial interaction, and have found that the prepared flagellin mutants have significantly enhanced TLR5-stimulating activity compared to that of prior (? wild type?) flagellin proteins, thereby completing the present invention.

Therefore, it is an object of the present invention to provide flagellin mutants having an enhanced activity of stimulating TLR5.

It is another object of the present invention to provide a vaccine adjuvant containing at least one of said flagellin mutants as an active ingredient.

Technical Solution

To achieve the above objects, the present invention provides flagellin mutants for suppressing the interaction between flagellin monomers in the TLR5 agonist flagellin.

Also, the present invention provides a vaccine adjuvant containing at least one of said flagellin mutants as an active ingredient.

Advantageous Effects

In the present invention, more improved flagellin vaccine adjuvants were developed by providing flagellin mutants having enhanced TLR-stimulating activity compared to that of a prior flagellin, which was found to show a potent mucosal vaccine adjuvant effect by stimulating TLR5 as disclosed in PCT International Patent Publication No. WO 2005/070455.

The flagellin mutants according to the present invention will be applied for the treatment of infectious diseases, autoimmune diseases, allergic diseases and the like, and furthermore, in anticancer therapy, and will provide an important ring connecting basic research with bedside clinical studies. Thus, the application of the inventive flagellin mutants to a variety of vaccine formulations can create very high added-value.

DESCRIPTION OF DRAWINGS

Figure 1:
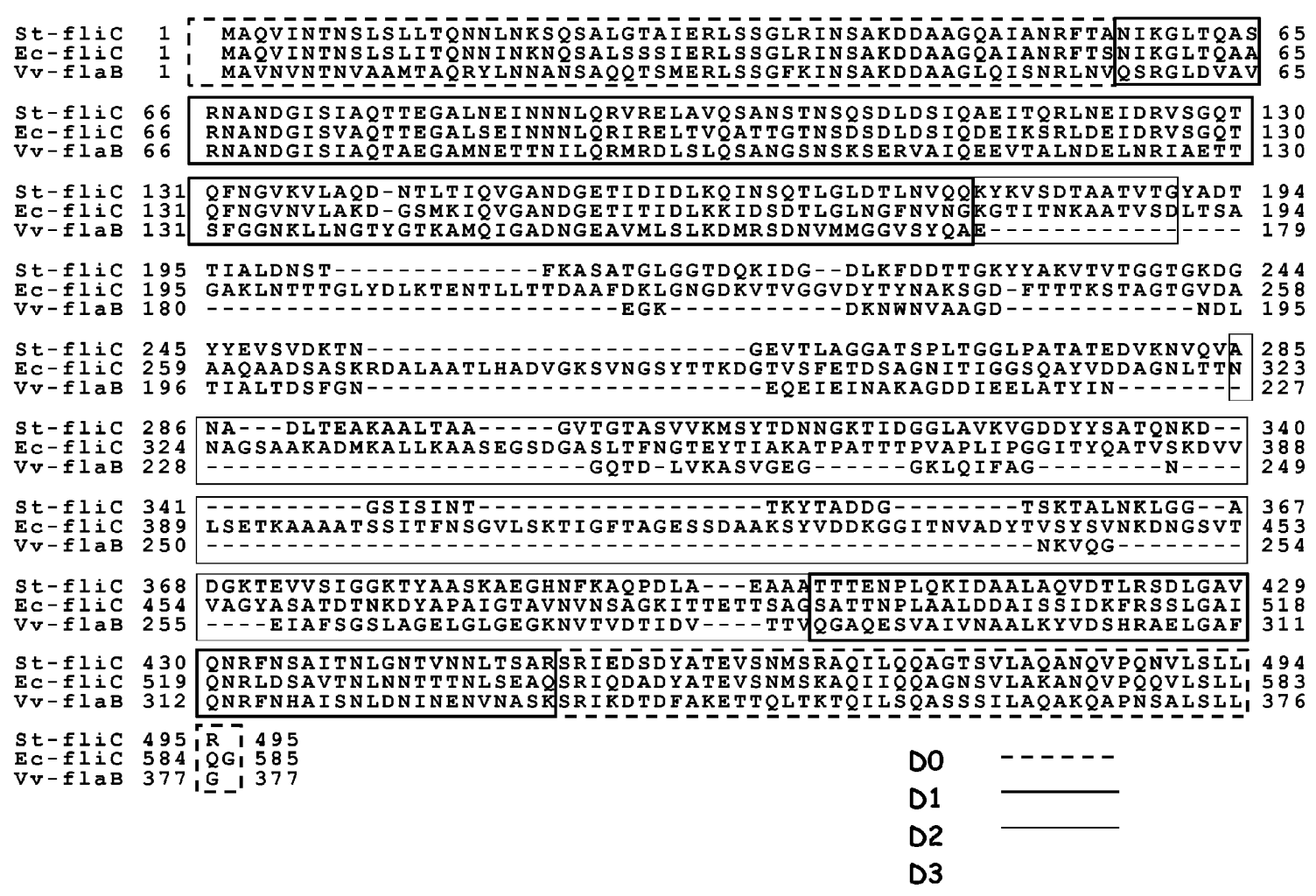

FIG. 1 shows the comparison of amino acid homology between the *Salmonella flagellin* St-FliC (SEQ ID NO: 45), the *E. coli* flagellin Ec-FliC (SEQ ID NO: 46) and the *V. vulnificus* flagellin Vv-FlaB (SEQ ID NO: 47), in which the domain of the flagellin protein of each bacterial strain is indicated as a box (Samatey F A, et al., Structure of the bacterial flagellar protofilament and implications for a switch for supercoiling. Nature. 2001 410(6826):331-7).

BEST MODE

Figure 2:
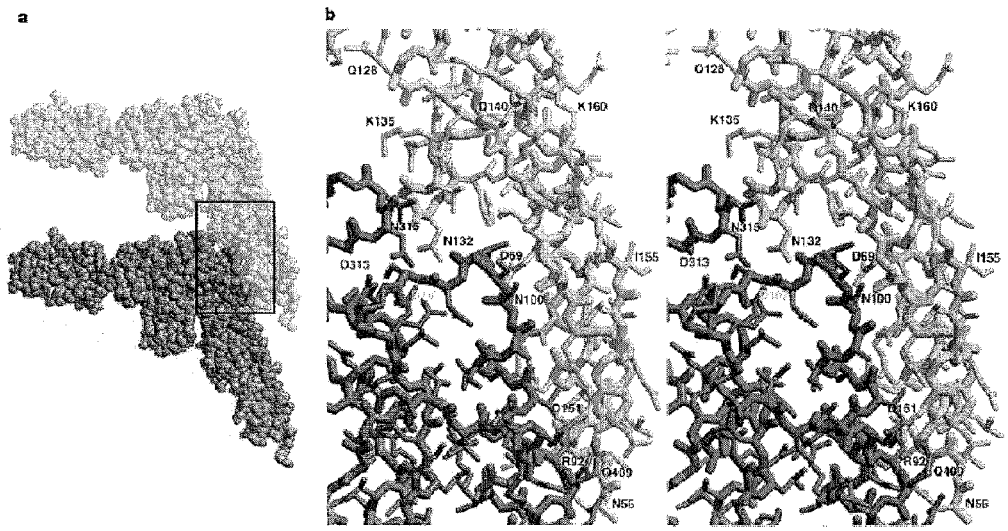
FIG. 2 is a schematic diagram showing a strategy inducing site-directed mutations in of the *V. vulnificus* flagellin gene flaB in the construction of the flagellin mutant according to the present invention (Samatey F A, et al., Structure of the bacterial flagellar protofilament and implications for a switch for supercoiling. Nature. 2001 410(6826):331-7).
Figure 2:
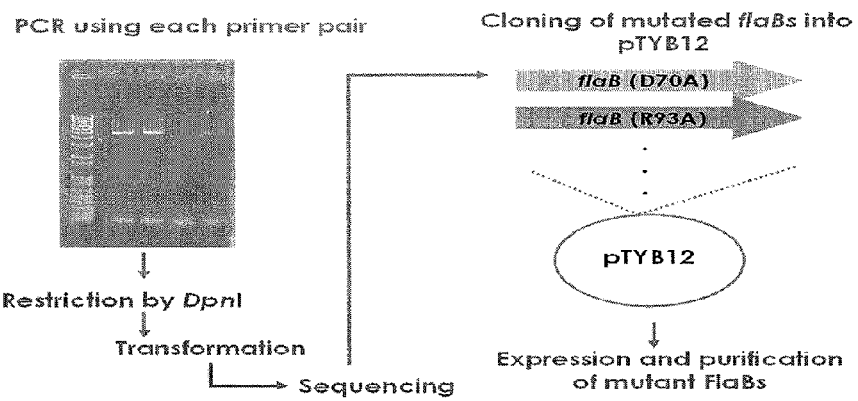

Hereinafter, the present invention will be described in further detail.

The present invention relates to flagellin mutants, prepared by point-mutating some of the amino acids of a TLR5 agonist flagellin, such that flagellin mutation suppress the multimerization of flagellin monomers, thus showing an enhanced activity of stimulating TLR5.

The present invention relates to: a flagellin mutant (D70A) of SEQ ID NO: 2, prepared by site-directed mutagenesis of aspartic acid (D70) to alanine (A) at position 70 of the wild-type *V. vulnificus* flagellin FlaB analyzed to be involved in the axial interaction between flagellin monomers in the TLR5 agonist flagellin; a flagellin mutant (R93A) of SEQ ID NO: 4, prepared by site-directed mutagenesis of arginine (R93) to alanine (A) at position 93; a flagellin mutant (L97W) of SEQ ID NO: 6, prepared by site-directed mutagenesis of leucine (L97) to tryptophan (W) at position 97; a flagellin mutant (N101A) of SEQ ID NO: 8, prepared by site-directed mutagenesis of asparagine (N101) to alanine (A) at position 101; a flagellin mutant (S103W) of SEQ ID NO: 10, prepared by site-directed mutagenesis of serine (S103) to tryptophan (W) at position 103; a flagellin mutant (E108A) of SEQ ID NO: 12, prepared by site-directed mutagenesis of glutamic acid (E108) to alanine (A) at position 108; a flagellin mutant (N135D) of SEQ ID NO: 14, prepared by site-directed mutagenesis of asparagine (N135) to aspartic acid (D) at position 135; a flagellin mutant (A151W) of SEQ ID NO: 16, prepared by site-directed mutagenesis of alanine (A151) to tryptophan (W) at position 151; a flagellin mutant (N153W) of SEQ ID NO: 18, prepared by site-directed mutagenesis of asparagine (N153) to tryptophan (W) at position 153; and a flagellin mutant (V291W) of SEQ ID NO: 20, prepared by site-directed mutagenesis of valine (V291) to tryptophan (W)

at position 291. Also, among the flagellin mutants, flagellin mutants having two or more amino acid substitutions fall within the scope of the present invention, and examples thereof may include a flagellin mutant (D70A/N135D) of SEQ ID NO: 44, prepared by site-directed mutagenesis of aspartic acid (D70) to alanine (A) at position 70 of the wild-type *V. vulnificus* flagellin FlaB, and asparagine (N135) to aspartic acid (D) at position 135, but the scope of the present invention is not limited thereto.

As used herein, the term "flagellins" refers to single molecules constituting flagella that determine the mobility of bacteria.

The flagellin mutants, provided according to the present invention, have a significantly enhanced activity of stimulating TLR5, and this phenomenon is because the flagellin mutants significantly reduce flagellin multimerization compared to prior flagellin mutants, thus suppressing flagellin polymerization.

Accordingly, the flagellin mutants having significantly enhanced TLR5-stimulating activity, prepared according to the present invention, can provide more potent TLR agonists as substitutes for the prior flagellins, thus providing vaccine adjuvants having increased efficiency compared to that of the prior flagellins.

A process of demonstrating the enhanced TLR5-stimulating activity of the flagellin mutants according to the present invention comprises the steps of:

1) preparing flagellin mutants of SEQ ID NOS: 2, 4, 6, 8, 10, 12, 14, 16, 18, 20 and 44;

2) confirming that the flagellin mutants suppress flagellin polymerization in an aqueous solution; and 3) confirming the TLR5 activation of each of recombinant flagellin mutants induced in *E. coli*.

Mode For Invention

Hereinafter, the present invention will be described in further detail with reference to examples and test examples. It is to be understood, however, that these examples and test examples are illustrative only, and the scope of the present invention is not limited thereto.

The characteristics of strains and plasmids, used in the present invention, are summarized in Table 1 below. A method of preparing each of flagellin mutants, and the detailed characteristics of each flagellin mutant, are shown in examples and test examples.

<Culture and Storage of Each Strain>

*E. coli* strains, used in the following examples and test examples, were cultured in Luria Bertani media (Difco Co.). The cultured strains were stored in 30% glycerol in a freezer at −80° C.

EXAMPLE 1

Preparation of Recombinant Flagellin Mutants by Site-directed Mutagenesis

According to the previously reported data of analysis for the three-dimensional structure of *Salmonella* flagellin (Yonekura K, Maki-Yonekura S, Namba K: Complete atomic model of the bacterial flagellar filament by electron cryomicroscopy. Nature. 2003 424(6949):643-50; Samatey F A, Imada K, Nagashima S, Vonderviszt F, Kumasaka T, Yamamoto M, Namba K: Structure of the bacterial flagellar protofilament and implications for a switch for supercoiling. Nature. 2001 410(6826):331-7), and the bioinformatics analysis conducted by the present inventors, amino acid residues required for the axial interaction between *V. vulnificus* flagellin FlaB monomers are as follows. That is, it was analyzed that aspartic acid (D70) at position 70 of the upper subunit of each monomer, which is involved in the axial interaction, asparagine (D135) at position 135 of the upper subunit, and alanine (A151) at position 153 of the upper subunit, form multimers through polar-charge reactions with asparagines (N100) at position 100 of the lower subunit of each monomer, glutamic acid (E108) at position 108 of the lower subunit, arginine (R93) at position 93 of the lower subunit and alanine (A292) at position of the lower subunit, respectively. That is, the polar-charge reactions occur between the following amino acid residues: upper flagellin D70 and lower flagellin N100; upper flagellin N135 and lower flagellin E107; upper flagellin A151 and lower flagellin R93; and upper flagellin N153 and lower flagellin A292.

In the present invention, the following flagellin mutants were prepared by site-directed mutagenesis of the following amino acid residues analyzed to be involved in the axial interaction between flagellin subunits: a flagellin mutant (D70A) of SEQ ID NO: 2, prepared by site-directed mutagenesis of aspartic acid (D70) to alanine (A) at position 70; a flagellin mutant (R93A) of SEQ ID NO: 4, prepared by site-directed mutagenesis of arginine (R93) to alanine (A) at position 93; a flagellin mutant (N101A) of SEQ ID NO: 8, prepared by site-directed mutagenesis of asparagine (N101) to alanine (A) at position 101; a flagellin mutant (E108A) of SEQ ID NO: 12, prepared by site-directed mutagenesis of

TABLE 1

| Strains or plasmids | Characteristics | Sources |
| --- | --- | --- |
| *Escherichia coli* | | |
| DH5α | F recA1; restriction negative | Our laboratory |
| ER2566 | F-λ-fhuA2[lon] ompT lacZ::T7 gene1 gal sulA11 (mcrC-mrr)114:IS10R(mcr-73::miniTn10-TetS)2 R(zgb-210::Tn10)(TetS) endA1 [dcm] | New England Biolab |
| BL21(DE3) | F-ompT $hsdS_{B(}r_B$-$m_B$-) gal dcm (DE3) | Novagen |
| Plasmids | | |
| pCR2.1 TOPO | PCR TA cloning vector, $Amp^R$, $Km^R$ | Invitrogen |
| pTYB12 | IMPACT (Intein Mediated Purification with an Affinity Chitin-binding Tag) expression vector, $Amp^R$ | New England Biolab | glutamic acid (E108) to alanine (A) at position 108; a flagellin mutant (N135D) of SEQ ID NO: 14, prepared by site-directed mutagenesis of asparagine (N135) to aspartic acid (D) at position 135; a flagellin mutant (A151W) of SEQ ID NO: 16, prepared by site-directed mutagenesis of alanine (A151) to tryptophan (W) at position 151; and a flagellin mutant (N153W) of SEQ ID NO: 18, prepared by site-directed mutagenesis of asparagine (N153) to tryptophan (W) at position 153. However, alanine (A292) at position 292, analyzed to be involved in the axial interaction between flagellin monomers, was excluded from the construction of mutants, because it was thought to not be changed even after it would be mutated.

In addition, the following mutants were prepared by site-directed mutagenesis of the following amino acid residues inferred to be involved in the axial interaction between flagellin monomers: a flagellin mutant (L97W) of SEQ ID NO: 6, prepared by site-directed mutagenesis of leucine (L97) to tryptophan (W) at position 97; a flagellin mutant (S103W) of SEQ ID NO: 10, prepared by site-directed mutagenesis of serine (S103) to tryptophan (W) at position 103; and a flagellin mutant (V291W) of SEQ ID NO: 20, prepared by site-directed mutagenesis of valine (V291) to tryptophan (W) at position 291.

First, in order to obtain template DNA for site-directed mutagenesis, a 1,142-bp DNA fragment containing the flaB gene ORF was amplified by PCR using a PCR primer FlaB-V5 of SEQ ID NO: 21 (5'-gcggccgcatggcagtgaatgtaaatgtaaatacaaac-3'; underlined portion: NotI restriction enzyme recognition site for cloning) and a PCR primer FlaB-V4 of SEQ ID NO: 22 (5'-cccggggcctagtagacttagcgctga-3'; underlined portion: SmaI restriction enzyme recognition site for cloning. The PCR amplification was performed using the primers FlaB-V5 and FlaB-V4 in the following conditions: initial denaturation at 95r for 1 min, and then 30 cycles of denaturation at 95r for 30 sec, annealing at 70r for 30 sec and extension at 72r for 1 min, followed by final extension at 72r for 10 min. The amplified flaB DNA fragment was cloned into a PCR 2.1-TOPO cloning vector (Invitrogen Co.), and the resulting vector was named "pCMM270". The pCMM270 plasmid was used as template DNA for subsequent site-directed mutagenesis.

PCR conditions and cloned plasmids for the construction of site-directed mutants of the *V. vulnificus* flagellin gene flaB are summarized in Table 2 below.

TABLE 2

| Mutation position | Primer (SEQ ID NO) | PCR annealing temperature | Name of pCR2.1-TOPO clone | Name of pTYB12 clone |
|---|---|---|---|---|
| D70A | FlaB-SD1 (SEQ ID NO: 23)<br>5'-gtacgtaacgccaacgcaggtatctcaatc-3'<br>FlaB-SD2 (SEQ ID NO: 24)<br>5'-gattgagatacctgcgttggcgttacgtac-3' | 63° C. | pCMM272 | pCMM276 |
| R93A | FlaB-SD13-2 (SEQ ID NO: 25)<br>5'-catcctacaacgtatggctgacctatctctacaatc-3'<br>FlaB-SD14-2 (SEQ ID NO: 26)<br>5'-gattgtagagataggtcagccatacgttgtaggatg-3' | 63° C. | pCMM281 | pCMM291 |
| L97W | FlaB-SD17 (SEQ ID NO: 27)<br>5'-gcgtgacctatcttggcaatccgcgaacgg-3'<br>FlaB-SD18 (SEQ ID NO: 28)<br>5'-ccgttcgcggattgccaagataggtcacgc-3' | 66° C. | pCMM282 | pCMM292 |
| N101A | FlaB-SD9-3 (SEQ ID NO: 29)<br>5'-ctacaatccgcggccggctcaaactcaaaatc-3'<br>FlaB-SD10-3 (SEQ ID NO: 30)<br>5'-gattttgagtttgagccggccgcggattgtag-3' | 64° C. | pCMM283 | pCMM293 |
| S103W | FlaB-SD15 (SEQ ID NO: 31)<br>5'-caatccgcgaacggctggaactcaaaatcag-3'<br>FlaB-SD16 (SEQ ID NO: 32)<br>5'-ctgattttgagttccagccgttcgcggattg-3' | 63° C. | pCMM284 | pCMM294 |
| E108A | FlaB-SD11 (SEQ ID NO: 33)<br>5'-caaactcaaaatcagcgcgcgtggcgattc-3'<br>FlaB-SD12 (SEQ ID NO: 34)<br>5'-gaatcgccacgcgcgctgattttgagtttg-3' | 63° C. | pCMM285 | pCMM295 |
| N135D | FlaB-SD3 (SEQ ID NO: 35)<br>5'-cgtcttttggtggtgacaagctgctaaacg-3'<br>FlaB-SD4 (SEQ ID NO: 36)<br>5'-cgtttagcagcttgtcaccaccaaaagacg-3' | 63° C. | pCMM273 | pCMM277 |
| A151W | FlaB-SD5 (SEQ ID NO: 37)<br>5'-gcaatgcaaattggttgggataacggtgaagcg-3'<br>FlaB-SD6 (SEQ ID NO: 38)<br>5'-cgcttcaccgttatcccaaccaatttgcattgc-3' | 63° C. | pCMM286 | pCMM296 |
| N153W | FlaB-SD7 (SEQ ID NO: 39)<br>5'-caaattggtgcggattggggtgaagcggtcatg-3'<br>FlaB-SD8 (서연번호 40)<br>5'-catgaccgcttcaccccaatccgcaccaatttg-3' | 67° C. | pCMM287 | pCMM297 |

TABLE 2-continued

| Mutation position | Primer (SEQ ID NO) | PCR annealing temperature | Name of pCR2.1-TOPO clone | Name of pTYB12 clone |
|---|---|---|---|---|
| V291W | FlaB-SD19 (SEQ ID NO: 41)<br>5'-gcgcaagagtcgtgggcgattgtggatgcg-3'<br>FlaB-SD20 (SEQ ID NO: 42)<br>5'-cgcatccacaatcgcccacgactcttgcgc-3' | 67° C. | pCMM288 | pCMM298 |
| D70A/N135D | FlaB-SD1 (SEQ ID NO: 23)<br>5'-gtacgtaacg ccaacgcagg tatctcaatc-3'<br>FlaB-SD2 (SEQ ID NO: 23)<br>5'-gattgagata cctgcgttgg cgttacgtac-3' | 63° C. | pCMM288 | pCMM298 |

In order to construct each of the site-directed mutant flaB DNAs (D70A, R93A, L97W, N101A, S103W, E108A, N135D, A151W, N153W, V291W and D70A/N135D), a mutant strand was synthesized by PCR reaction using each of the primer pairs shown in Table 2 above, pCMM270 as a PCR template, and a proofreading Pfu polymerase in accordance with the manufacturer's instruction (Stratagene Co.). Each of the PCR reactions was performed in the following conditions: initial denaturation at 95° C. for 45 sec, and then 16 cycles of denaturation at 95° C. for 45 sec, annealing for 1 min at the temperature shown in Table 2, and extension at 68° C. for min, followed by final extension at 68° C. for 10 min. Each of the amplified site-directed mutant flaB DNAs of SEQ ID NOs: 1, 3, 5, 7, 9, 11, 13, 15, 17 and 19 was cloned into a PCR 2.1-TOPO cloning vector, and the resulting vectors were named "pCMM272", "pCMM281", "pCMM282", "pCMM283", "pCMM284", "pCMM285", "pCMM273", "pCMM286", "pCMM287" and "pCMM288" (Table 2).

To prepare a D70A/N135D dual site-directed mutant flagellin D70A/N135D of SEQ ID NO: 44, pCMM273 with flaB DNA was used as a template for PCR reaction. The mutant strand (D70A) was synthesized by PCR using a PCR primer FlaB-SD1 of SEQ ID NO: 23, a PCR primer FlaB-SD2 of SEQ ID NO: 24 and a proofreading Pfu polymerase in accordance with the manufacturer's instruction (Stratagene Co.). The PCR reaction was performed in the following condition: initial denaturation at 95r for 45 sec, and then 16 cycles of denaturation at 95r for 45 sec, annealing at 63r for 1 min and extension at 68r for 10 min, followed by final extension at 68r for 10 min. The amplified D70A/N135D dual site-directed mutant flaB DNA of SEQ ID NO: 43 was named "pCMM274".

Each of the DNA fragments of SEQ ID NOS: 1, 3, 5, 7, 9, 11, 13, 15, 17 and 19, containing the site-directed mutant flaB genes (D70A, R93A, L97W, N101A, S103W, E108A, N135D, A151W, N153W, V291W and D70A/N135D), were digested with restriction enzymes NotI and SmaI, and then cloned into a pTYB12 plasmid (New England Biolabs) digested with the same restriction enzymes. The resulting plasmids were named "pCMM276", "pCMM291", "pCMM292", "pCMM293", "pCMM293", "pCMM294", "pCMM295", "pCMM277", "pCMM296", "pCMM297", "pCMM298" and "pCMM278", respectively. These plasmids were electroporated into E. coli ER2566, and 0.5 mM of 5-bromo-indole-3-chloro-isopropyl-β-D-glactopyranoside (IPTG) was added thereto to induce the expression of the mutant flagellin genes. Point mutant flagellin (D70A, R93A, L97W, N101A, S103W, E108A, N135D, A151W, N153W, V291W and D70A/N135D) proteins were obtained from intein fusion proteins using 1,4-dithiothreitol (1,4-DTT) and a chitin bead column according to the manufacturer's instruction. Before use, endotoxin contained in the isolated point mutant proteins was removed using AffinityPak™ Detoxi Gel™ Endotoxin Removing gel (Pirece). The isolated recombinant proteins were subjected to gel filtration using a Superdex 120 column (AKTA-Prime, Amersham), thus purifying the recombinant flagellin mutants of SEQ ID NOS: 2, 4, 6, 8, 10, 12, 14, 16, 18, 20 and 44 with high purity.

TEST EXAMPLE 1

Production of Recombinant Flagellin Mutants and Biochemical Properties Thereof in Aqueous Solution In order to prepare recombinant flagellin mutants, each of the genes of SEQ ID NOS: SEQ ID NOS: 1, 3, 5, 7, 9, 11, 13, 15, 17, 19 and 43, encoding the flagellin mutants, was cloned into a pTYB12 plasmid, and then transfected into E. coli ER2566. 0.3 mM IPTG (isopropyl-β-D-1-thiogalactoside) was added to the media to induce the production of recombinant flagellin mutants, and then, the resulting proteins were analyzed by SDS-polyacrylamide gel electrophoresis and native-gel electrophoresis. The analysis results are shown in FIGS. 3 and 4.

Figure 3:
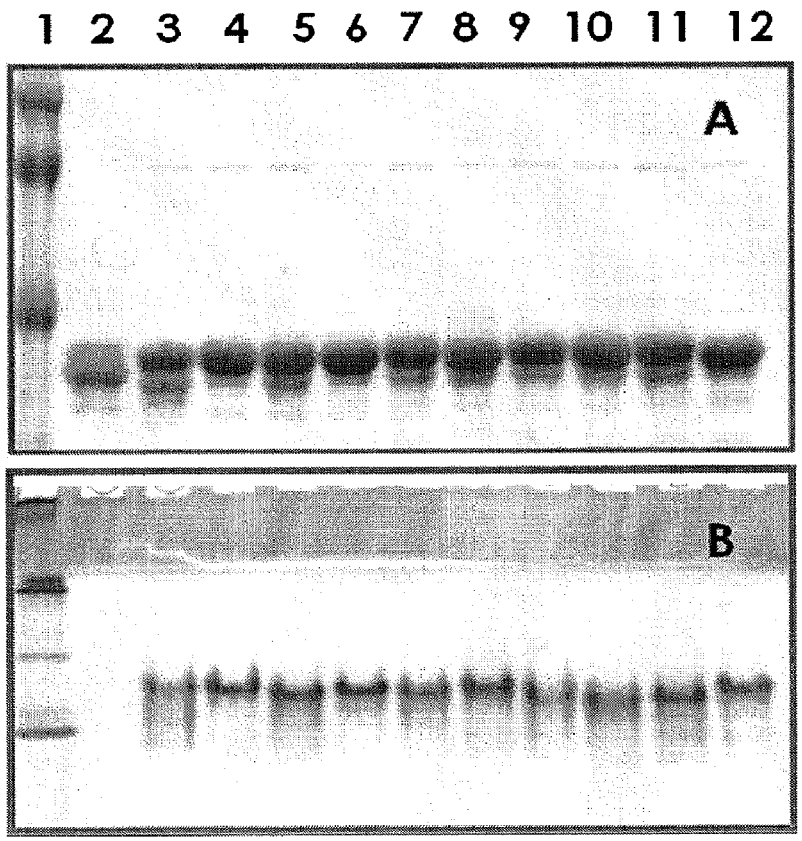
FIGS. 3 and 4 show the effect of the inventive recombinant flagellin mutant on flagellin polymerization in an aqueous solution.
Figure 4:
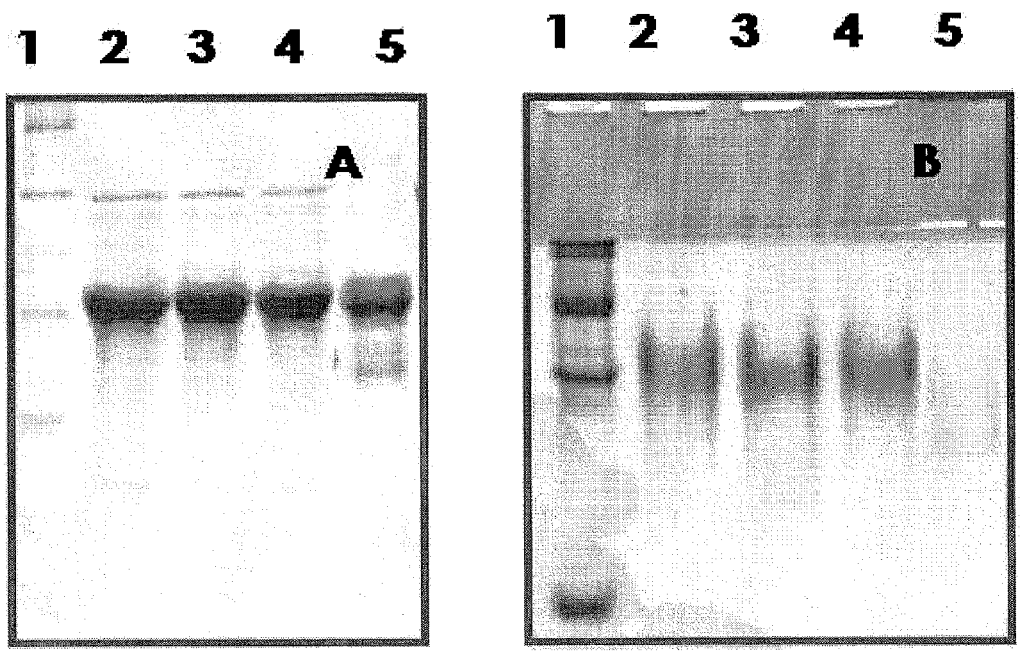

As shown in FIGS. 3 and 4, which show the results of SDS-PAGE analysis of the wild-type flagellin (FlaB) and the mutated flagellin FlaB, the point-mutated flagellin proteins (D70A, R93A, L97W, N101A, S103W, E108A, N135D, A151W, N153W, V291W and D70A/N135D) of SEQ ID NOS: 2, 4, 6, 8, 10, 12, 14, 16, 18, 20 and 44, and the wild-type flagellin (FlaB) protein, all showed a major band at 41.5 kDa. In the results of native-gel electrophoresis, it was observed that the wild-type FlaB protein formed a huge multimer, so that most of the protein remained in the stacking gel, and some of the FlaB protein, introduced into the resolving gel, was distributed between 66 kDa and 140 kDa. However, the point-mutated flagellin proteins (D70A, R93A, L97W, N101A, S103W, E108A, N135D, A151W, N153W, V291W and D70A/N135D) according to the present invention formed multimers at about 140 kDa. The above results suggest that the wild-type FlaB protein formed a huge multimer in an aqueous solution, but the point-mutated flagellin mutants (D70A, R93A, L97W, N101A, S103W, E108A, N135D, A151W, N153W, V291W and D70A/N135D) according to the present invention were present as multimers having a size smaller than that of the wild-type flagellin protein. Accordingly, it could be confirmed that the inventive flagellin mutants (D70A, R93A, L97W, N101A, S103W, E108A, N135D, A151W, N153W, V291W and D70A/N135D) of SEQ ID NOS: 2, 4, 6, 8, 10, 12, 14, 16, 18, 20 and 44 suppressed the polymerization of flagellin.

TEST EXAMPLE 2

TLR5-Stimulating Activity of Flagellin Mutants

Figure 5:
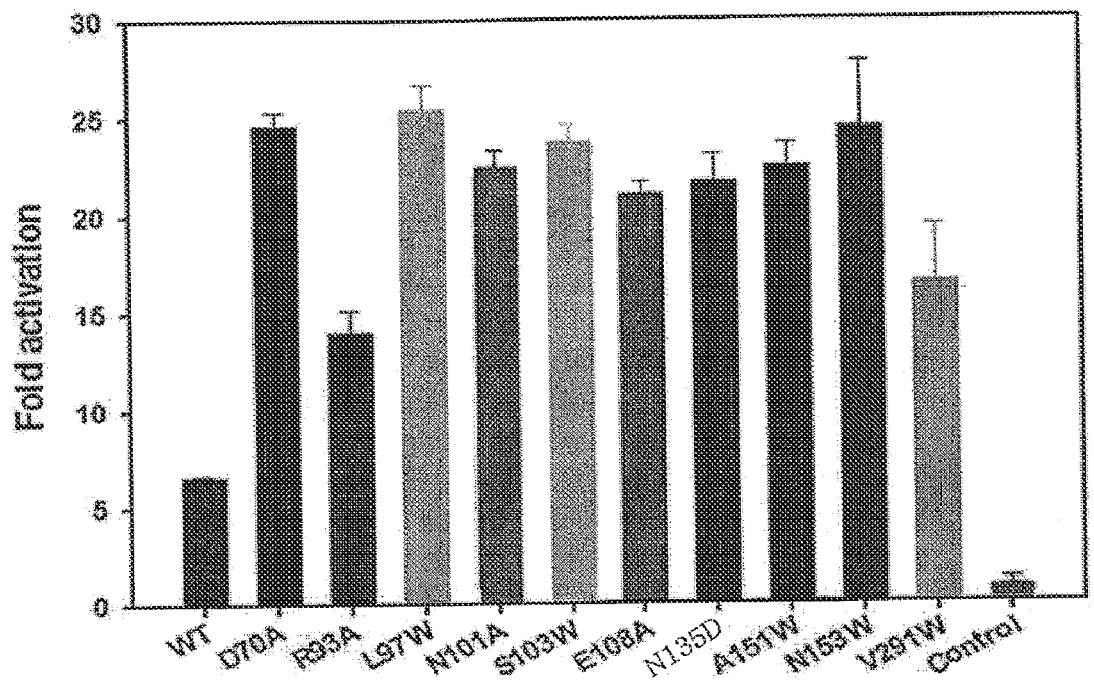
FIGS. 5 and 6 are graphic diagrams showing the measurement results of TLR-stimulating activity of the flagellin mutant according to the present invention.
Figure 6:
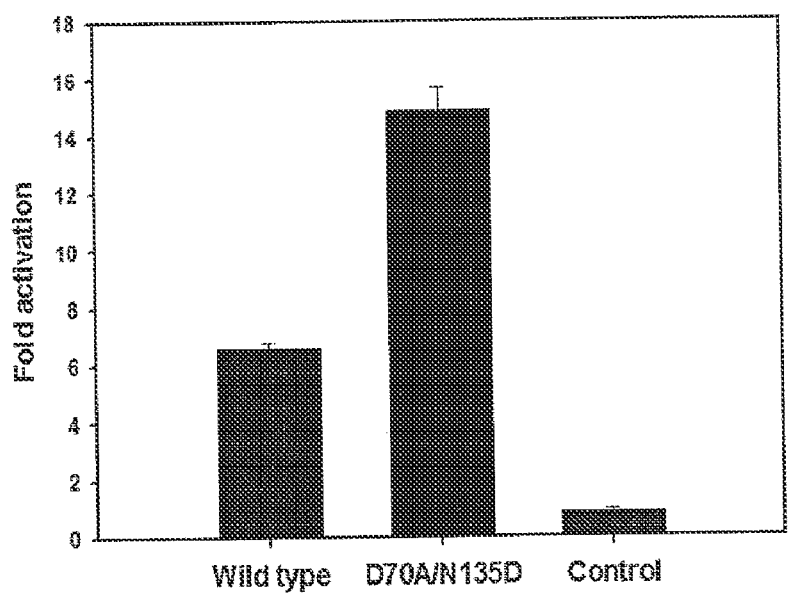

In order to measure the transcriptional activity of NF-κB, involved in TLR5-mediated signaling, so as to determine the TLR5-stimulating activities of the wild-type FlaB and the inventive flagellin mutants of SEQ ID NOS: 2, 4, 6, 8, 10, 12, 14, 16, 18, 20 and 44, 293T cells were dispensed into each well of 24-well plates at a density of $1 \times 10^5$ cells/well and cultured overnight. Then, a reporter plasmid NF-κB-Luc (provided by professor Jeong-Mok Kim, Institute of Biomedical Science, Hanyang University College of Medicine, Korea) enabling transcriptional activity to be observed, a TLR5 gene-cloned p3xFlag-hTLR5 plasmid (provided by Dr. Steven B. Mizel, Departments of Microbiology and Immunology, Wake Forest University School of Medicine, USA) and a beta-galactosidase expression plasmid (Clontech) were simultaneously introduced into the cells using FuGENE6 (Roche). After the cells were additionally cultured for 24 hours, the cultures were replaced with fresh media, and the cells were treated with the flagellin mutants (D70A, R93A, L97W, N101A, S103W, E108A, N135D, A151W, N153W, V291W and D70A/N135D) of SEQ ID NOS: 2, 4, 6, 8, 10, 12, 14, 16, 18, 20 and 44, isolated in Example 1, for 18-24 hours. Then, the transcription of NF-κB in the cells was assayed by measuring the luciferase activity using a luminometer (Berthold), and the measurement results are shown in FIGS. 5 and 6. As shown in FIGS. 5 and 6, the group treated with 20 ng/ml of the wild-type FlaB protein showed an increase in TLR5-mediated NF-κB transcription activity of about 6.6 fold compared to the control group treated only with phosphate-buffered solution. However, the groups treated with 20 ng/ml of each of the recombinant flagellin FlaB mutants (D70A, R93A, L97W, N101A, S103W, E108A, N135D, A151W, N153W, V291W and D70A/N135D) showed increases in TLR5-mediated NF-κB transcription activity of about 24.6 fold, 14 fold, 25 fold, 22.6 fold, 23.7 fold, 21 fold, 21.7 fold, 22.5 fold, 24.5 fold, 16.6 fold and 14.9 fold, respectively, compared to the control group treated only with phosphate-buffered solution.

[Sequence List Text]

SEQ ID NOS: 1 and 2 are the gene and amino acid sequences of a flagellin mutant (D70A), prepared by site-directed mutagenesis of aspartic acid (D70) to alanine (A) at position 70 of the *V. vulnificus* flagellin FlaB.

SEQ ID NOS: 3 and 4 are the gene and amino acid sequences of a flagellin mutant (R93A), prepared by site-directed mutagenesis of arginine (R93) to alanine (A) at position 93 of the *V. vulnificus* flagellin FlaB.

SEQ ID NOS: 5 and 6 are the gene and amino acid sequences of a flagellin mutant (L97W), prepared by site-directed mutagenesis of leucine (L97) to tryptophan (W) at position 97 of the *V. vulnificus* flagellin FlaB.

SEQ ID NOS: 7 and 8 are the gene and amino acid sequences of a flagellin mutant (N101A), prepared by site-directed mutagenesis of asparagine (N101) to alanine (A) at position 101 of the *V. vulnificus* flagellin FlaB.

SEQ ID NOS: 9 and 10 are the gene and amino acid sequences of a flagellin mutant (S103W), prepared by site-directed mutagenesis of serine (S103) to tryptophan (W) at position 103 of the *V. vulnificus* flagellin FlaB.

SEQ ID NOS: 11 and 12 are the gene and amino acid sequences of a flagellin mutant (E108A), prepared by site-directed mutagenesis of glutamic acid (E108) to alanine (A) at position 108 of the *V. vulnificus* flagellin FlaB.

SEQ ID NOS: 13 and 14 are the gene and amino acid sequences of a flagellin mutant (N135D), prepared by site-directed mutagenesis of asparagine (N135) to aspartic acid (D) at position 135 of the *V. vulnificus* flagellin FlaB.

SEQ ID NOS: 15 and 16 are the gene and amino acid sequences of a flagellin mutant (A151W), prepared by site-directed mutagenesis of alanine (A151) to tryptophan (W) at position 151 of the *V. vulnificus* flagellin FlaB.

SEQ ID NOS: 17 and 18 are the gene and amino acid sequences of a flagellin mutant (N153W), prepared by site-directed mutagenesis of asparagine (N153) to tryptophan (W) at position 153 of the *V. vulnificus* flagellin FlaB.

SEQ ID NOS: 19 and 20 are the gene and amino acid sequences of a flagellin mutant (V291W), prepared by site-directed mutagenesis of valine (V291) to tryptophan (W) at position 291 of the *V. vulnificus* flagellin FlaB.

SEQ ID NOS: 21 to 42 are primer sequences used in the flagellin mutants of SEQ ID NOS: 2, 4, 6, 8, 10, 12, 14, 16, 18, 20 and 44.

SEQ ID NOS: 43 and 44 are the gene and amino acid sequences of a flagellin mutant (D70A/N135D), prepared by site-directed mutagenesis of aspartic acid (D70) to alanine (A) at position 70 of the *V. vulnificus* flagellin FlaB, and asparagine (N135) to aspartic acid (D) at position 135 of the *V. vulnificus* flagellin FlaB.

The invention claimed is:

1. An isolated *Vibrio vulnificus* flagellin mutant having enhanced toll-like receptor (TLR-5)-stimulating activity, wherein the mutant is the flagellin mutant (A151W) of SEQ ID NO: 16, prepared by site-directed mutagenesis of alanine (A151) to tryptophan (W) at position 151 of the *V. vulnificus* flagellin FlaB.

2. A vaccine adjuvant containing, as an active ingredient, the isolated flagellin mutant of SEQ ID NO: 16.

3. A method for stimulating the activity of a toll-like receptor-5 (TLR5), comprising contacting a host cell with the isolated flagellin mutant of SEQ ID NO: 16, thereby stimulating TLR5 activity.

4. The method of claim 3, wherein the contacting comprises introducing the flagellin mutant into the host cell.

5. A method for stimulating the activity of a toll-like receptor-5 (TLR5) in a subject, comprising administering a composition comprising the isolated flagellin mutant of SEQ ID NO: 16 to the subject.

* * * * *

SEQUENCE LISTING

```
<160> NUMBER OF SEQ ID NOS: 47

<210> SEQ ID NO 1
<211> LENGTH: 1134
<212> TYPE: DNA
<213> ORGANISM: Vibrio vulnificus

<400> SEQUENCE: 1
atggcagtga atgtaaatac aaacgtagca gcaatgacag cacagcgtta cctgaataac      60
gcaaacagcg cacaacaaac ttcgatggag cgtctgtctt caggtttcaa aatcaacagt     120
gcaaaagatg acgcagccgg tctgcaaatc tctaaccgct tgaacgtaca aagtcgcggt     180
ctagacgttg cggtacgtaa cgccaacgca ggtatctcaa tcgcacaaac cgcagaaggt     240
gcgatgaacg agaccaccaa catcctacaa cgtatgcgtg acctatctct acaatccgcg     300
```

```
aacggctcaa actcaaaatc agagcgcgtg gcgattcaag aagaagtgac agcattgaat    360
gacgagctaa accgtattgc agaaaccacg tcttttggtg gtaacaagct gctaaacggt    420
acttacggca cgaaagcaat gcaaattggt gcggataacg gtgaagcggt catgctttca    480
ctgaaagaca tgcgctctga caacgtgatg atgggcggcg tgagctacca agctgaagaa    540
ggcaaagaca agaactggaa tgtggccgca ggcgacaacg acttgacgat tgcactgaca    600
gacagctttg gtaacgagca agagatcgaa atcaacgcga aagcgggtga tgacatcgaa    660
gagctagcga cgtacatcaa cggtcaaact gaccttgtaa aagcgtcagt gggtgaaggc    720
ggcaagctac agatctttgc tggtaacaac aaagttcaag gtgaaattgc tttctcaggt    780
agcctagctg gtgaacttgg cctaggcgaa ggcaaaaacg tcacggtaga cacgattgac    840
gtgacaaccg tacaaggtgc gcaagagtcg gtagcgattg tggatgcggc actgaaatac    900
gtagacagcc accgtgcaga gctgggtgca ttccagaacc gtttcaacca tgcaatcagc    960
aacttggaca catcaacga aaacgtgaac gcgtcgaaga gccgaatcaa agataccgac   1020
ttcgcgaaag aaacgactca gttgaccaag acacaaattc tatcgcaagc atcaagttcc   1080
attcttgcgc aagcgaaaca agcgccaaac tcagcgctaa gtctactagg ctaa         1134
```

<210> SEQ ID NO 2
<211> LENGTH: 377
<212> TYPE: PRT
<213> ORGANISM: Vibrio vulnificus

<400> SEQUENCE: 2

```
Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Ala Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Leu Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
    130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240
```

Gly Lys Leu Gln Ile Phe Ala Gly Asn Asn Lys Val Gln Glu Ile
                245                 250                 255

Ala Phe Ser Gly Ser Leu Ala Gly Glu Leu Gly Leu Gly Glu Gly Lys
                260                 265                 270

Asn Val Thr Val Asp Thr Ile Asp Val Thr Thr Val Gln Gly Ala Gln
                275                 280                 285

Glu Ser Val Ala Ile Val Asp Ala Ala Leu Lys Tyr Val Asp Ser His
290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
                340                 345                 350

Ile Leu Ser Gln Ala Ser Ser Ser Ile Leu Ala Gln Ala Lys Gln Ala
                355                 360                 365

Pro Asn Ser Ala Leu Ser Leu Leu Gly
            370                 375

<210> SEQ ID NO 3
<211> LENGTH: 1134
<212> TYPE: DNA
<213> ORGANISM: Vibrio vulnificus

<400> SEQUENCE: 3

```
atggcagtga atgtaaatac aaacgtagca gcaatgacag cacagcgtta cctgaataac      60
gcaaacagcg cacaacaaac ttcgatggag cgtctgtctt caggtttcaa aatcaacagt     120
gcaaaagatg acgcagccgg tctgcaaatc tctaaccgct tgaacgtaca agtcgcggt     180
ctagacgttg cggtacgtaa cgccaacgac ggtatctcaa tcgcacaaac cgcagaaggt     240
gcgatgaacg agaccaccaa catcctacaa cgtatggctg acctatctct acaatccgcg     300
aacggctcaa actcaaaatc agagcgcgtg gcgattcaag aagaagtgac agcattgaat     360
gacgagctaa ccgtattgc agaaaccacg tcttttggtg gtaacaagct gctaaacggt     420
acttacggca cgaaagcaat gcaaattggt gcggataacg tgaagcggt catgctttca     480
ctgaaagaca tgcgctctga caacgtgatg atgggcggcg tgagctacca agctgaagaa     540
ggcaaagaca gaactggaa tgtggccgca ggcgacaacg acttgacgat tgcactgaca     600
gacagctttg gtaacgagca agagatcgaa atcaacgcga aagcgggtga tgacatcgaa     660
gagctagcga cgtacatcaa cggtcaaact gaccttgtaa aagcgtcagt gggtgaaggc     720
ggcaagctac agatctttgc tggtaacaac aaagttcaag gtgaaattgc tttctcaggt     780
agcctagctg gtgaacttgg cctaggcgaa ggcaaaaacg tcacggtaga cacgattgac     840
gtgacaaccg tacaaggtgc gcaagagtcg gtagcgattg tggatgcggc actgaaatac     900
gtagacagcc accgtgcaga gctgggtgca ttccagaacc gtttcaacca tgcaatcagc     960
aacttggaca acatcaacga aaacgtgaac gcgtcgaaga gccgaatcaa agataccgac    1020
ttcgcgaaag aaacgactca gttgaccaag acacaaattc tatcgcaagc atcaagttcc    1080
attcttgcgc aagcgaaaca agcgccaaac tcagcgctaa gtctactagg ctaa          1134
```

<210> SEQ ID NO 4
<211> LENGTH: 377
<212> TYPE: PRT
<213> ORGANISM: Vibrio vulnificus

<400> SEQUENCE: 4

```
Met Ala Val Asn Val Asn Thr Asn Val Ala Met Thr Ala Gln Arg
  1               5                  10                  15

Tyr Leu Asn Asn Ala Asn Ser Ala Gln Gln Thr Ser Met Glu Arg Leu
                 20                  25                  30

Ser Ser Gly Phe Lys Ile Asn Ser Ala Lys Asp Asp Ala Ala Gly Leu
             35                  40                  45

Gln Ile Ser Asn Arg Leu Asn Val Gln Ser Arg Gly Leu Asp Val Ala
     50                  55                  60

Val Arg Asn Ala Asn Asp Gly Ile Ser Ile Ala Gln Thr Ala Glu Gly
 65                  70                  75                  80

Ala Met Asn Glu Thr Thr Asn Ile Leu Gln Arg Met Ala Asp Leu Ser
                 85                  90                  95

Leu Gln Ser Ala Asn Gly Ser Asn Ser Lys Ser Glu Arg Val Ala Ile
                100                 105                 110

Gln Glu Glu Val Thr Ala Leu Asn Asp Glu Leu Asn Arg Ile Ala Glu
            115                 120                 125

Thr Thr Ser Phe Gly Gly Asn Lys Leu Leu Asn Gly Thr Tyr Gly Thr
    130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
                180                 185                 190

Asn Asp Leu Thr Ile Ala Leu Thr Asp Ser Phe Gly Asn Glu Gln Glu
            195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
                260                 265                 270

Asn Val Thr Val Asp Thr Ile Asp Val Thr Thr Val Gln Gly Ala Gln
            275                 280                 285

Glu Ser Val Ala Ile Val Asp Ala Ala Leu Lys Tyr Val Asp Ser His
    290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
                340                 345                 350

Ile Leu Ser Gln Ala Ser Ser Ser Ile Leu Ala Gln Ala Lys Gln Ala
            355                 360                 365

Pro Asn Ser Ala Leu Ser Leu Leu Gly
    370                 375
```

<210> SEQ ID NO 5
<211> LENGTH: 1134
<212> TYPE: DNA
<213> ORGANISM: Vibrio vulnificus -continued

```
<400> SEQUENCE: 5
atggcagtga atgtaaatac aaacgtagca gcaatgacag cacagcgtta cctgaataac    60
gcaaacagcg cacaacaaac ttcgatggag cgtctgtctt caggtttcaa aatcaacagt   120
gcaaaagatg acgcagccgg tctgcaaatc tctaaccgct tgaacgtaca aagtcgcggt   180
ctagacgttg cggtacgtaa cgccaacgac ggtatctcaa tcgcacaaac cgcagaaggt   240
gcgatgaacg agaccaccaa catcctacaa cgtatgcgtg acctatcttg caatccgcg    300
aacggctcaa actcaaaatc agagcgcgtg gcgattcaag aagaagtgac agcattgaat   360
gacgagctaa accgtattgc agaaaccacg tcttttggtg gtaacaagct gctaaacggt   420
acttacggca cgaaagcaat gcaaattggt gcggataacg gtgaagcggt catgctttca   480
ctgaaagaca tgcgctctga caacgtgatg atgggcggcg tgagctacca agctgaagaa   540
ggcaaagaca agaactggaa tgtggccgca ggcgacaacg acttgacgat gcactgaca    600
gacagctttg gtaacgagca agagatcgaa atcaacgcga aagcgggtga tgacatcgaa   660
gagctagcga cgtacatcaa cggtcaaact gaccttgtaa aagcgtcagt gggtgaaggc   720
ggcaagctac agatctttgc tggtaacaac aaagttcaag gtgaaattgc tttctcaggt   780
agcctagctg gtgaacttgg cctaggcgaa ggcaaaaacg tcacggtaga cacgattgac   840
gtgacaaccg tacaaggtgc gcaagagtcg gtagcgattg tggatgcggc actgaaatac   900
gtagacagcc accgtgcaga gctgggtgca ttccagaacc gtttcaacca tgcaatcagc   960
aacttggaca catcaacga aaacgtgaac gcgtcgaaga gccgaatcaa agataccgac   1020
ttcgcgaaag aaacgactca gttgaccaag acacaaattc tatcgcaagc atcaagttcc   1080
attcttgcgc aagcgaaaca agcgccaaac tcagcgctaa gtctactagg ctaa         1134

<210> SEQ ID NO 6
<211> LENGTH: 377
<212> TYPE: PRT
<213> ORGANISM: Vibrio vulnificus

<400> SEQUENCE: 6

Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Trp Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
    130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175
```

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Ile Glu Glu Leu Ala Thr
210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Lys Val Gln Gly Glu Ile
            245                 250                 255

Ala Phe Ser Gly Ser Leu Ala Gly Glu Leu Gly Leu Gly Glu Gly Lys
                260                 265                 270

Asn Val Thr Val Asp Thr Ile Asp Val Thr Thr Val Gln Gly Ala Gln
            275                 280                 285

Glu Ser Val Ala Ile Val Asp Ala Ala Leu Lys Tyr Val Asp Ser His
        290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350

Ile Leu Ser Gln Ala Ser Ser Ser Ile Leu Ala Gln Ala Lys Gln Ala
        355                 360                 365

Pro Asn Ser Ala Leu Ser Leu Leu Gly
            370                 375

<210> SEQ ID NO 7
<211> LENGTH: 1134
<212> TYPE: DNA
<213> ORGANISM: Vibrio vulnificus

<400> SEQUENCE: 7
atggcagtga atgtaaatac aaacgtagca gcaatgacag cacagcgtta cctgaataac      60
gcaaacagcg cacaacaaac ttcgatggag cgtctgtctt caggtttcaa atcaacagt     120 gcaaaagatg acgcagccgg tctgcaaatc tctaaccgct tgaacgtaca agtcgcggt     180 ctagacgttg cggtacgtaa cgccaacgac ggtatctcaa tcgcacaaac cgcagaaggt     240
gcgatgaacg agaccaccaa catcctacaa cgtatgcgtg acctatctct acaatccgcg     300
gccggctcaa actcaaaatc agagcgcgtg gcgattcaag aagaagtgac agcattgaat     360
gacgagctaa accgtattgc agaaaccacg tcttttggtg gtaacaagct gctaaacggt     420
acttacggca cgaaagcaat gcaaattggt gcggataacg gtgaagcggt catgctttca     480
ctgaaagaca tgcgctctga caacgtgatg atgggcggcg tgagctacca agctgaagaa     540
ggcaaagaca agaactggaa tgtggccgca ggcgacaacg acttgacgat tgcactgaca     600
gacagctttg gtaacgagca agagatcgaa atcaacgcga agcgggtga tgacatcgaa     660 gagctagcga cgtacatcaa cggtcaaact gaccttgtaa aagcgtcagt gggtgaaggc     720
ggcaagctac agatctttgc tggtaacaac aaagttcaag gtgaaattgc tttctcaggt     780
agcctagctg gtgaacttgg cctaggcgaa ggcaaaaacg tcacggtaga cacgattgac     840
gtgacaaccg tacaaggtgc gcaagagtcg gtagcgattg tggatgcggc actgaaatac     900
gtagacagcc accgtgcaga gctgggtgca ttccagaacc gtttcaacca tgcaatcagc     960

```
aacttggaca acatcaacga aaacgtgaac gcgtcgaaga gccgaatcaa agataccgac   1020
ttcgcgaaag aaacgactca gttgaccaag acacaaattc tatcgcaagc atcaagttcc   1080
attcttgcgc aagcgaaaca agcgccaaac tcagcgctaa gtctactagg ctaa         1134
```

<210> SEQ ID NO 8
<211> LENGTH: 377
<212> TYPE: PRT
<213> ORGANISM: Vibrio vulnificus

<400> SEQUENCE: 8

```
Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Leu Gln Ser Ala Ala Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
    130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285

Glu Ser Val Ala Ile Val Asp Ala Ala Leu Lys Tyr Val Asp Ser His
    290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350
```

Ile Leu Ser Gln Ala Ser Ser Ile Leu Ala Gln Ala Lys Gln Ala
        355                 360                 365

Pro Asn Ser Ala Leu Ser Leu Leu Gly
        370                 375

<210> SEQ ID NO 9
<211> LENGTH: 1134
<212> TYPE: DNA
<213> ORGANISM: Vibrio vulnificus

<400> SEQUENCE: 9
atggcagtga atgtaaatac aaacgtagca gcaatgacag cacagcgtta cctgaataac      60
gcaaacagcg cacaacaaac ttcgatggag cgtctgtctt caggtttcaa aatcaacagt     120
gcaaaagatg acgcagccgg tctgcaaatc tctaaccgct tgaacgtaca agtcgcggt     180 ctagacgttg cggtacgtaa cgccaacgac ggtatctcaa tcgcacaaac cgcagaaggt     240
gcgatgaacg agaccaccaa catcctacaa cgtatgcgtg acctatctct acaatccgcg     300
aacggctgga actcaaaatc agagcgcgtg gcgattcaag aagaagtgac agcattgaat     360
gacgagctaa accgtattgc agaaaccacg tcttttggtg gtaacaagct gctaaacggt     420
acttacggca cgaaagcaat gcaaattggt gcggataacg gtgaagcggt catgctttca     480
ctgaaagaca tgcgctctga caacgtgatg atgggcggcg tgagctacca agctgaagaa     540
ggcaaagaca agaactggaa tgtggccgca ggcgacaacg acttgacgat tgcactgaca     600
gacagctttg gtaacgagca agagatcgaa atcaacgcga aagcgggtga tgacatcgaa     660
gagctagcga cgtacatcaa cggtcaaact gaccttgtaa aagcgtcagt gggtgaaggc     720
ggcaagctac agatctttgc tggtaacaac aaagttcaag gtgaaattgc tttctcaggt     780
agcctagctg gtgaacttgg cctaggcgaa ggcaaaaacg tcacggtaga cacgattgac     840
gtgacaaccg tacaaggtgc gcaagagtcg gtagcgattg tggatgcggc actgaaatac     900
gtagacagcc accgtgcaga gctgggtgca ttccagaacc gtttcaacca tgcaatcagc     960
aacttggaca catcaacga aaacgtgaac gcgtcgaaga gccgaatcaa agataccgac    1020
ttcgcgaaag aaacgactca gttgaccaag acacaaattc tatcgcaagc atcaagttcc    1080
attcttgcgc aagcgaaaca agcgccaaac tcagcgctaa gtctactagg ctaa          1134

<210> SEQ ID NO 10
<211> LENGTH: 377
<212> TYPE: PRT
<213> ORGANISM: Vibrio vulnificus

<400> SEQUENCE: 10

Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
            85                  90                  95

Leu Gln Ser Ala Asn Gly Trp Asn Ser Lys Ser Glu Arg Val Ala Ile
            100                 105                 110

```
Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285

Glu Ser Val Ala Ile Val Asp Ala Ala Leu Lys Tyr Val Asp Ser His
    290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350

Ile Leu Ser Gln Ala Ser Ser Ser Ile Leu Ala Gln Ala Lys Gln Ala
        355                 360                 365

Pro Asn Ser Ala Leu Ser Leu Leu Gly
    370                 375

<210> SEQ ID NO 11
<211> LENGTH: 1134
<212> TYPE: DNA
<213> ORGANISM: Vibrio vulnificus

<400> SEQUENCE: 11
atggcagtga atgtaaatac aaacgtagca gcaatgacag cacagcgtta cctgaataac      60
gcaaacagcg cacaacaaac ttcgatggag cgtctgtctt caggtttcaa aatcaacagt     120
gcaaaagatg acgcagccgg tctgcaaatc tctaaccgct tgaacgtaca agtcgcggt      180 ctagacgttg cggtacgtaa cgccaacgac ggtatctcaa tcgcacaaac cgcagaaggt     240
gcgatgaacg agaccaccaa catcctacaa cgtatgcgtg acctatctct acaatccgcg     300
aacggctcaa actcaaaatc agcgcgcgtg gcgattcaag aagaagtgac agcattgaat     360
gacgagctaa accgtattgc agaaaccacg tcttttggtg gtaacaagct gctaaacggt     420
acttacggca cgaaagcaat gcaaattggt gcggataacg gtgaagcggt catgctttca     480
ctgaaagaca tgcgctctga caacgtgatg atgggcggcg tgagctacca agctgaagaa     540
ggcaaagaca agaactggaa tgtggccgca ggcgacaacg acttgacgat tgcactgaca     600
```

```
gacagctttg gtaacgagca agagatcgaa atcaacgcga aagcgggtga tgacatcgaa    660
gagctagcga cgtacatcaa cggtcaaact gaccttgtaa aagcgtcagt gggtgaaggc    720
ggcaagctac agatctttgc tggtaacaac aaagttcaag gtgaaattgc tttctcaggt    780
agcctagctg tgaacttggg cctaggcgaa ggcaaaaacg tcacggtaga cacgattgac    840
gtgacaaccg tacaaggtgc gcaagagtcg gtagcgattg tggatgcggc actgaaatac    900
gtagacagcc accgtgcaga gctgggtgca ttccagaacc gtttcaacca tgcaatcagc    960
aacttggaca catcaacga aaacgtgaac gcgtcgaaga gccgaatcaa agataccgac   1020
ttcgcgaaag aaacgactca gttgaccaag acacaaattc tatcgcaagc atcaagttcc   1080
attcttgcgc aagcgaaaca agcgccaaac tcagcgctaa gtctactagg ctaa         1134
```

<210> SEQ ID NO 12
<211> LENGTH: 377
<212> TYPE: PRT
<213> ORGANISM: Vibrio vulnificus

<400> SEQUENCE: 12

```
Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Leu Gln Ser Ala Asn Gly Ser Asn Ser Lys Ser Ala Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
    130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285
```

```
Glu Ser Val Ala Ile Val Asp Ala Ala Leu Lys Tyr Val Asp Ser His
        290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
                340                 345                 350

Ile Leu Ser Gln Ala Ser Ser Ile Leu Ala Gln Ala Lys Gln Ala
            355                 360                 365

Pro Asn Ser Ala Leu Ser Leu Leu Gly
    370                 375

<210> SEQ ID NO 13
<211> LENGTH: 1134
<212> TYPE: DNA
<213> ORGANISM: Vibrio vulnificus

<400> SEQUENCE: 13
atggcagtga atgtaaatac aaacgtagca gcaatgacag cacagcgtta cctgaataac      60
gcaaacagcg cacaacaaac ttcgatggag cgtctgtctt caggtttcaa atcaacagt     120 gcaaaagatg acgcagccgg tctgcaaatc tctaaccgct tgaacgtaca agtcgcggt     180 ctagacgttg cggtacgtaa cgccaacgac ggtatctcaa tcgcacaaac cgcagaaggt     240
gcgatgaacg agaccaccaa catcctacaa cgtatgcgtg acctatctct acaatccgcg     300
aacggctcaa actcaaaatc agagcgcgtg gcgattcaag aagaagtgac agcattgaat     360
gacgagctaa accgtattgc agaaaccacg tcttttggtg gtgacaagct gctaaacggt     420
acttacggca cgaaagcaat gcaaattggt gcggataacg tgaagcggt catgctttca     480 ctgaaagaca tgcgctctga caacgtgatg atgggcggcg tgagctacca agctgaagaa     540
ggcaaagaca agaactggaa tgtggccgca ggcgacaaca cttgacgat tgcactgaca     600 gacagctttg gtaacgagca agagatcgaa atcaacgcga agcgggtga tgacatcgaa     660 gagctagcga cgtacatcaa cggtcaaact gaccttgtaa agcgtcagt gggtgaaggc     720 ggcaagctac agatctttgc tggtaacaac aaagttcaag gtgaaattgc tttctcaggt     780
agcctagctg tgaacttggg cctaggcgaa ggcaaaaacg tcacggtaga cacgattgac     840
gtgacaaccg tacaaggtgc gcaagagtcg gtagcgattg tggatgcggc actgaaatac     900
gtagacagcc accgtgcaga gctgggtgca ttccagaacc gtttcaacca tgcaatcagc     960
aacttggaca acatcaacga aaacgtgaac gcgtcgaaga gccgaatcaa agataccgac    1020
ttcgcgaaag aaacgactca gttgaccaag acacaaattc tatcgcaagc atcaagttcc    1080
attcttgcgc aagcgaaaca agcgccaaac tcagcgctaa gtctactagg ctaa          1134

<210> SEQ ID NO 14
<211> LENGTH: 377
<212> TYPE: PRT
<213> ORGANISM: Vibrio vulnificus

<400> SEQUENCE: 14

Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45
```

Gln Ile Ser Asn Arg Leu Asn Val Gln Ser Arg Gly Leu Asp Val Ala
    50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Leu Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asp Lys Leu Leu Asn Gly Thr Tyr Gly Thr
130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285

Glu Ser Val Ala Ile Val Asp Ala Ala Leu Lys Tyr Val Asp Ser His
    290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350

Ile Leu Ser Gln Ala Ser Ser Ser Ile Leu Ala Gln Ala Lys Gln Ala
        355                 360                 365

Pro Asn Ser Ala Leu Ser Leu Leu Gly
    370                 375

<210> SEQ ID NO 15
<211> LENGTH: 1134
<212> TYPE: DNA
<213> ORGANISM: Vibrio vulnificus

<400> SEQUENCE: 15
atggcagtga atgtaaatac aaacgtagca gcaatgacag cacagcgtta cctgaataac      60
gcaaacagcg cacaacaaac ttcgatggag cgtctgtctt caggtttcaa aatcaacagt     120
gcaaaagatg acgcagccgg tctgcaaatc tctaaccgct tgaacgtaca aagtcgcggt     180
ctagacgttg cggtacgtaa cgccaacgac ggtatctcaa tcgcacaaac cgcagaaggt     240

```
gcgatgaacg agaccaccaa catcctacaa cgtatgcgtg acctatctct acaatccgcg    300
aacggctcaa actcaaaatc agagcgcgtg gcgattcaag aagaagtgac agcattgaat    360
gacgagctaa accgtattgc agaaaccacg tcttttggtg gtaacaagct gctaaacggt    420
acttacggca cgaaagcaat gcaaattggt tgggataacg gtgaagcggt catgctttca    480
ctgaaagaca tgcgctctga caacgtgatg atgggcggcg tgagctacca agctgaagaa    540
ggcaaagaca agaactggaa tgtggccgca ggcgacaacg acttgacgat tgcactgaca    600
gacagctttg gtaacgagca agagatcgaa atcaacgcga aagcgggtga tgacatcgaa    660
gagctagcga cgtacatcaa cggtcaaact gaccttgtaa agcgtcagt gggtgaaggc    720 ggcaagctac agatctttgc tggtaacaac aaagttcaag gtgaaattgc tttctcaggt    780
agcctagctg gtgaacttgg cctaggcgaa ggcaaaaacg tcacggtaga cacgattgac    840
gtgacaaccg tacaaggtgc gcaagagtcg gtagcgattg tggatgcggc actgaaatac    900
gtagacagcc accgtgcaga gctgggtgca ttccagaacc gtttcaacca tgcaatcagc    960
aacttggaca acatcaacga aaacgtgaac gcgtcgaaga gccgaatcaa agataccgac   1020
ttcgcgaaag aaacgactca gttgaccaag acacaaattc tatcgcaagc atcaagttcc   1080
attcttgcgc aagcgaaaca agcgccaaac tcagcgctaa gtctactagg ctaa         1134
```

<210> SEQ ID NO 16
<211> LENGTH: 377
<212> TYPE: PRT
<213> ORGANISM: Vibrio vulnificus

<400> SEQUENCE: 16

```
Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Leu Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
    130                 135                 140

Lys Ala Met Gln Ile Gly Trp Asp Asn Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220
```

```
Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
            245                 250                 255

Ala Phe Ser Gly Ser Leu Ala Gly Glu Leu Gly Leu Gly Glu Gly Lys
        260                 265                 270

Asn Val Thr Val Asp Thr Ile Asp Val Thr Thr Val Gln Gly Ala Gln
    275                 280                 285

Glu Ser Val Ala Ile Val Asp Ala Ala Leu Lys Tyr Val Asp Ser His
290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350

Ile Leu Ser Gln Ala Ser Ser Ser Ile Leu Ala Gln Ala Lys Gln Ala
        355                 360                 365

Pro Asn Ser Ala Leu Ser Leu Leu Gly
    370                 375
```

<210> SEQ ID NO 17
<211> LENGTH: 1134
<212> TYPE: DNA
<213> ORGANISM: Vibrio vulnificus

<400> SEQUENCE: 17

```
atggcagtga atgtaaatac aaacgtagca gcaatgacag cacagcgtta cctgaataac     60
gcaaacagcg cacaacaaac ttcgatggag cgtctgtctt caggtttcaa aatcaacagt    120
gcaaaagatg acgcagccgg tctgcaaatc tctaaccgct tgaacgtaca aagtcgcggt    180
ctagacgttg cggtacgtaa cgccaacgac ggtatctcaa tcgcacaaac cgcagaaggt    240
gcgatgaacg agaccaccaa catcctacaa cgtatgcgtg acctatctct acaatccgcg    300
aacggctcaa actcaaaatc agagcgcgtg gcgattcaag aagaagtgac agcattgaat    360
gacgagctaa accgtattgc agaaaccacg tcttttggtg gtaacaagct gctaaacggt    420
acttacggca cgaaagcaat gcaaattggt gcggattggg gtgaagcggt catgctttca    480
ctgaaagaca tgcgctctga caacgtgatg atgggcggcg tgagctacca agctgaagaa    540
ggcaaagaca agaactggaa tgtggccgca ggcgacaacg acttgacgat gcactgaca     600
gacagctttg gtaacgagca agagatcgaa atcaacgcga aagcgggtga tgacatcgaa    660
gagctagcga cgtacatcaa cggtcaaact gaccttgtaa aagcgtcagt gggtgaaggc    720
ggcaagctac agatctttgc tggtaacaac aaagttcaag gtgaaattgc tttctcaggt    780
agcctagctg gtgaacttgg cctaggcgaa ggcaaaaacg tcacggtaga cacgattgac    840
gtgacaaccg tacaaggtgc gcaagagtcg gtagcgattg tggatgcggc actgaaatac    900
gtagacagcc accgtgcaga gctgggtgca ttccagaacc gtttcaacca tgcaatcagc    960
aacttggaca acatcaacga aaacgtgaac gcgtcgaaga gccgaatcaa agataccgac   1020
ttcgcgaaag aaacgactca gttgaccaag acacaaattc tatcgcaagc atcaagttcc   1080
attcttgcgc aagcgaaaca agcgccaaac tcagcgctaa gtctactagg ctaa          1134
```

<210> SEQ ID NO 18
<211> LENGTH: 377
<212> TYPE: PRT

<213> ORGANISM: Vibrio vulnificus

<400> SEQUENCE: 18

```
Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Leu Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
    130                 135                 140

Lys Ala Met Gln Ile Gly Ala Asp Trp Gly Glu Ala Val Met Leu Ser
145                 150                 155                 160

Leu Lys Asp Met Arg Ser Asp Asn Val Met Met Gly Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
        195                 200                 205

Ile Glu Ile Asn Ala Lys Ala Gly Asp Asp Ile Glu Glu Leu Ala Thr
    210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285

Glu Ser Val Ala Ile Val Asp Ala Ala Leu Lys Tyr Val Asp Ser His
    290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350

Ile Leu Ser Gln Ala Ser Ser Ile Leu Ala Gln Ala Lys Gln Ala
        355                 360                 365

Pro Asn Ser Ala Leu Ser Leu Leu Gly
    370                 375
```

<210> SEQ ID NO 19
<211> LENGTH: 1134
<212> TYPE: DNA

<213> ORGANISM: Vibrio vulnificus

<400> SEQUENCE: 19

```
atggcagtga atgtaaatac aaacgtagca gcaatgacag cacagcgtta cctgaataac      60
gcaaacagcg cacaacaaac ttcgatggag cgtctgtctt caggtttcaa aatcaacagt     120
gcaaaagatg acgcagccgg tctgcaaatc tctaaccgct tgaacgtaca agtcgcggt      180
ctagacgttg cggtacgtaa cgccaacgac ggtatctcaa tcgcacaaac cgcagaaggt     240
gcgatgaacg agaccaccaa catcctacaa cgtatgcgtg acctatctct acaatccgcg     300
aacggctcaa actcaaaatc agagcgcgtg gcgattcaag aagaagtgac agcattgaat     360
gacgagctaa accgtattgc agaaaccacg tcttttggtg gtaacaagct gctaaacggt     420
acttacggca cgaaagcaat gcaaattggt gcggataacg gtgaagcggt catgcttcca     480
ctgaaagaca tgcgctctga acgtgatg atgggcggcg tgagctacca agctgaagaa      540
ggcaaagaca agaactggaa tgtggccgca ggcgacaacg acttgacgat tgcactgaca     600
gacagctttg gtaacgagca agagatcgaa atcaacgcga agcgggtga tgacatcgaa      660
gagctagcga cgtacatcaa cggtcaaact gaccttgtaa agcgtcagt gggtgaaggc      720
ggcaagctac agatctttgc tggtaacaac aaagttcaag gtgaaattgc tttctcaggt     780
agcctagctg gtgaacttgg cctaggcgaa ggcaaaaacg tcacggtaga cacgattgac     840
gtgacaaccg tacaaggtgc gcaagagtcg tgggcgattg tggatgcggc actgaaatac     900
gtagacagcc accgtgcaga gctgggtgca ttccagaacc gtttcaacca tgcaatcagc     960
aacttggaca acatcaacga aaacgtgaac gcgtcgaaga gccgaatcaa agataccgac    1020
ttcgcgaaag aaacgactca gttgaccaag acacaaattc tatcgcaagc atcaagttcc    1080
attcttgcgc aagcgaaaca agcgccaaac tcagcgctaa gtctactagg ctaa          1134
```

<210> SEQ ID NO 20
<211> LENGTH: 377
<212> TYPE: PRT
<213> ORGANISM: Vibrio vulnificus

<400> SEQUENCE: 20

```
Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95

Leu Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
        115                 120                 125

Thr Thr Ser Phe Gly Gly Asn Lys Leu Leu Asn Gly Thr Tyr Gly Thr
    130                 135                 140

Lys Ala Met Gln Ile Gly Ala Asp Asn Gly Glu Ala Val Met Leu Ser
145                 150                 155                 160
```

```
Leu Lys Asp Met Arg Ser Asp Asn Val Met Met Gly Val Ser Tyr
            165                 170                 175
Gln Ala Glu Glu Gly Lys Asp Lys Asn Trp Asn Val Ala Ala Gly Asp
        180                 185                 190
Asn Asp Leu Thr Ile Ala Leu Thr Asp Ser Phe Gly Asn Glu Gln Glu
        195                 200                 205
Ile Glu Ile Asn Ala Lys Ala Gly Asp Asp Ile Glu Glu Leu Ala Thr
        210                 215                 220
Tyr Ile Asn Gly Gln Thr Asp Leu Val Lys Ala Ser Val Gly Glu Gly
225                 230                 235                 240
Gly Lys Leu Gln Ile Phe Ala Gly Asn Asn Lys Val Gln Gly Glu Ile
            245                 250                 255
Ala Phe Ser Gly Ser Leu Ala Gly Glu Leu Gly Leu Gly Glu Gly Lys
            260                 265                 270
Asn Val Thr Val Asp Thr Ile Asp Val Thr Thr Val Gln Gly Ala Gln
            275                 280                 285
Glu Ser Trp Ala Ile Val Asp Ala Ala Leu Lys Tyr Val Asp Ser His
        290                 295                 300
Arg Ala Glu Leu Gly Ala Phe Gln Asn Arg Phe Asn His Ala Ile Ser
305                 310                 315                 320
Asn Leu Asp Asn Ile Asn Glu Asn Val Asn Ala Ser Lys Ser Arg Ile
            325                 330                 335
Lys Asp Thr Asp Phe Ala Lys Glu Thr Thr Gln Leu Thr Lys Thr Gln
            340                 345                 350
Ile Leu Ser Gln Ala Ser Ser Ser Ile Leu Ala Gln Ala Lys Gln Ala
            355                 360                 365
Pro Asn Ser Ala Leu Ser Leu Leu Gly
        370                 375

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 21
gcggccgcat ggcagtgaat gtaaatgtaa atacaaac                            38

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 22 cccgggcct agtagactta gcgctga                                         27

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 23
gtacgtaacg ccaacgcagg tatctcaatc                                     30
```

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 24
gattgagata cctgcgttgg cgttacgtac                                    30

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 25
catcctacaa cgtatggctg acctatctct acaatc                             36

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 26
gattgtagag ataggtcagc catacgttgt aggatg                             36

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 27
gcgtgaccta tcttggcaat ccgcgaacgg                                    30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 28
ccgttcgcgg attgccaaga taggtcacgc                                    30

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 29
ctacaatccg cggccggctc aaactcaaaa tc                                 32

```
<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 30
gattttgagt ttgagccggc cgcggattgt ag                                32

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 31
caatccgcga acggctggaa ctcaaaatca g                                 31

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 32
ctgattttga gttccagccg ttcgcggatt g                                 31

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 33
caaactcaaa atcagcgcgc gtggcgattc                                   30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 34
gaatcgccac gcgcgctgat tttgagtttg                                   30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 35
cgtcttttgg tggtgacaag ctgctaaacg                                   30

<210> SEQ ID NO 36
<211> LENGTH: 30
```

```
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 36
cgtttagcag cttgtcacca ccaaaagacg                                       30

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 37
gcaatgcaaa ttggttggga taacggtgaa gcg                                   33

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 38
cgcttcaccg ttatcccaac caatttgcat tgc                                   33

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 39
caaattggtg cggattgggg tgaagcggtc atg                                   33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 40
catgaccgct tcaccccaat ccgcaccaat ttg                                   33

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 41
gcgcaagagt cgtgggcgat tgtggatgcg                                       30

<210> SEQ ID NO 42
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      construct

<400> SEQUENCE: 42
cgcatccaca atcgcccacg actcttgcgc                                          30

<210> SEQ ID NO 43
<211> LENGTH: 1134
<212> TYPE: DNA
<213> ORGANISM: Vibrio vulnificus

<400> SEQUENCE: 43
atggcagtga atgtaaatac aaacgtagca gcaatgacag cacagcgtta cctgaataac         60
gcaaacagcg cacaacaaac ttcgatggag cgtctgtctt caggtttcaa aatcaacagt        120
gcaaaagatg acgcagccgg tctgcaaatc tctaaccgct tgaacgtaca aagtcgcggt        180
ctagacgttg cggtacgtaa cgccaacgca ggtatctcaa tcgcacaaac cgcagaaggt        240
gcgatgaacg agaccaccaa catcctacaa cgtatgcgtg acctatctct acaatccgcg        300
aacggctcaa actcaaaatc agagcgcgtg gcgattcaag aagaagtgac agcattgaat        360
gacgagctaa accgtattgc agaaaccacg tcttttggtg gtgacaagct gctaaacggt        420
acttacggca cgaaagcaat gcaaattggt gcggataacg gtgaagcggt catgctttca        480
ctgaaagaca tgcgctctga caacgtgatg atgggcggcg tgagctacca agctgaagaa        540
ggcaaagaca gaactggaa tgtggccgca ggcgacaacg acttgacgat gcactgaca         600 gacagctttg gtaacgagca agagatcgaa atcaacgcga agcgggtga tgacatcgaa         660 gagctagcga cgtacatcaa cggtcaaact gaccttgtaa aagcgtcagt gggtgaaggc        720
ggcaagctac agatctttgc tggtaacaac aaagttcaag gtgaaattgc tttctcaggt        780
agcctagctg gtgaacttgg cctaggcgaa ggcaaaaacg tcacggtaga cacgattgac        840
gtgacaaccg tacaaggtgc gcaagagtcg gtagcgattg tggatgcggc actgaaatac        900
gtagacagcc accgtgcaga gctgggtgca ttccagaacc gtttcaacca tgcaatcagc        960
aacttggaca acatcaacga aaacgtgaac gcgtcgaaga gccgaatcaa agataccgac       1020
ttcgcgaaag aaacgactca gttgaccaag acacaaattc tatcgcaagc atcaagttcc       1080
attcttgcgc aagcgaaaca agcgccaaac tcagcgctaa gtctactagg ctaa             1134

<210> SEQ ID NO 44
<211> LENGTH: 377
<212> TYPE: PRT
<213> ORGANISM: Vibrio vulnificus

<400> SEQUENCE: 44

Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Asp Ala Ala Gly Leu
        35                  40                  45

Gln Ile Ser Asn Arg Leu Asn Val Gln Ser Arg Gly Leu Asp Val Ala
    50                  55                  60

Val Arg Asn Ala Asn Ala Gly Ile Ser Ile Ala Gln Thr Ala Glu Gly
65                  70                  75                  80

Ala Met Asn Glu Thr Thr Asn Ile Leu Gln Arg Met Arg Asp Leu Ser
                85                  90                  95
```

```
Leu Gln Ser Ala Asn Gly Ser Asn Ser Lys Ser Glu Arg Val Ala Ile
                100                 105                 110

Gln Glu Glu Val Thr Ala Leu Asn Asp Glu Leu Asn Arg Ile Ala Glu
            115                 120                 125

Thr Thr Ser Phe Gly Gly Asp Lys Leu Leu Asn Gly Thr Tyr Gly Thr
    130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Val Ser Tyr
                165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
    195                 200                 205

Ile Glu Ile Asn Ala Lys Ala Gly Asp Asp Ile Glu Glu Leu Ala Thr
210                 215                 220

Tyr Ile Asn Gly Gln Thr Asp Leu Val Lys Ala Ser Val Gly Glu Gly
225                 230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
    275                 280                 285

Glu Ser Val Ala Ile Val Asp Ala Ala Leu Lys Tyr Val Asp Ser His
290                 295                 300

Arg Ala Glu Leu Gly Ala Phe Gln Asn Arg Phe Asn His Ala Ile Ser
305                 310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
            340                 345                 350

Ile Leu Ser Gln Ala Ser Ser Ser Ile Leu Ala Gln Ala Lys Gln Ala
    355                 360                 365

Pro Asn Ser Ala Leu Ser Leu Leu Gly
    370                 375

<210> SEQ ID NO 45
<211> LENGTH: 495
<212> TYPE: PRT
<213> ORGANISM: Salmonella sp.

<400> SEQUENCE: 45

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95
```

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
                245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
                325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380

Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
                485                 490                 495

<210> SEQ ID NO 46
<211> LENGTH: 585
<212> TYPE: PRT
<213> ORGANISM: Escherichia coli

<400> SEQUENCE: 46

```
Met Ala Gln Val Ile Asn Thr Asn Ser Leu Ser Leu Ile Thr Gln Asn
1               5                   10                  15

Asn Ile Asn Lys Asn Gln Ser Ala Leu Ser Ser Ser Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ala Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Ile Arg Glu Leu Thr
                85                  90                  95

Val Gln Ala Thr Thr Gly Thr Asn Ser Asp Ser Asp Leu Asp Ser Ile
            100                 105                 110

Gln Asp Glu Ile Lys Ser Arg Leu Asp Glu Ile Asp Arg Val Ser Gly
        115                 120                 125

Gln Thr Gln Phe Asn Gly Val Asn Val Leu Ala Lys Asp Gly Ser Met
    130                 135                 140

Lys Ile Gln Val Gly Ala Asn Asp Gly Glu Thr Ile Thr Ile Asp Leu
145                 150                 155                 160

Lys Lys Ile Asp Ser Asp Thr Leu Gly Leu Asn Gly Phe Asn Val Asn
                165                 170                 175

Gly Lys Gly Thr Ile Thr Asn Lys Ala Ala Thr Val Ser Asp Leu Thr
            180                 185                 190

Ser Ala Gly Ala Lys Leu Asn Thr Thr Thr Gly Leu Tyr Asp Leu Lys
        195                 200                 205

Thr Glu Asn Thr Leu Leu Thr Thr Asp Ala Ala Phe Asp Lys Leu Gly
    210                 215                 220

Asn Gly Asp Lys Val Thr Val Gly Gly Val Asp Tyr Thr Tyr Asn Ala
225                 230                 235                 240

Lys Ser Gly Asp Phe Thr Thr Thr Lys Ser Thr Ala Gly Thr Gly Val
                245                 250                 255

Asp Ala Ala Gln Ala Ala Asp Ser Ala Ser Lys Arg Asp Ala Leu
            260                 265                 270

Ala Ala Thr Leu His Ala Asp Val Gly Lys Ser Val Asn Gly Ser Tyr
        275                 280                 285

Thr Thr Lys Asp Gly Thr Val Ser Phe Glu Thr Asp Ser Ala Gly Asn
    290                 295                 300

Ile Thr Ile Gly Gly Ser Gln Ala Tyr Val Asp Asp Ala Gly Asn Leu
305                 310                 315                 320

Thr Thr Asn Asn Ala Gly Ser Ala Ala Lys Ala Asp Met Lys Ala Leu
                325                 330                 335

Leu Lys Ala Ala Ser Glu Gly Ser Asp Gly Ala Ser Leu Thr Phe Asn
            340                 345                 350

Gly Thr Glu Tyr Thr Ile Ala Lys Ala Thr Pro Ala Thr Thr Pro
        355                 360                 365

Val Ala Pro Leu Ile Pro Gly Gly Ile Thr Tyr Gln Ala Thr Val Ser
    370                 375                 380

Lys Asp Val Val Leu Ser Glu Thr Lys Ala Ala Ala Thr Ser Ser
385                 390                 395                 400

Ile Thr Phe Asn Ser Gly Val Leu Ser Lys Thr Ile Gly Phe Thr Ala
                405                 410                 415
```

```
Gly Glu Ser Ser Asp Ala Ala Lys Ser Tyr Val Asp Lys Gly Gly
            420                 425                 430

Ile Thr Asn Val Ala Asp Tyr Thr Val Ser Tyr Ser Val Asn Lys Asp
            435                 440                 445

Asn Gly Ser Val Thr Val Ala Gly Tyr Ala Ser Ala Thr Asp Thr Asn
        450                 455                 460

Lys Asp Tyr Ala Pro Ala Ile Gly Thr Ala Val Asn Val Asn Ser Ala
465                 470                 475                 480

Gly Lys Ile Thr Thr Glu Thr Thr Ser Ala Gly Ser Ala Thr Thr Asn
            485                 490                 495

Pro Leu Ala Ala Leu Asp Asp Ala Ile Ser Ser Ile Asp Lys Phe Arg
            500                 505                 510

Ser Ser Leu Gly Ala Ile Gln Asn Arg Leu Asp Ser Ala Val Thr Asn
            515                 520                 525

Leu Asn Asn Thr Thr Thr Asn Leu Ser Glu Ala Gln Ser Arg Ile Gln
        530                 535                 540

Asp Ala Asp Tyr Ala Thr Glu Val Ser Asn Met Ser Lys Ala Gln Ile
545                 550                 555                 560

Ile Gln Gln Ala Gly Asn Ser Val Leu Ala Lys Ala Asn Gln Val Pro
            565                 570                 575

Gln Gln Val Leu Ser Leu Leu Gln Gly
            580                 585

<210> SEQ ID NO 47
<211> LENGTH: 377
<212> TYPE: PRT
<213> ORGANISM: Vibrio vulnificus

<400> SEQUENCE: 47

Met Ala Val Asn Val Asn Thr Asn Val Ala Ala Met Thr Ala Gln Arg
1               5                   10                  15

Tyr Leu Asn Asn Ala Asn Ser Ala Gln Gln Thr Ser Met Glu Arg Leu
            20                  25                  30

Ser Ser Gly Phe Lys Ile Asn Ser Ala Lys Asp Ala Ala Gly Leu
            35                  40                  45

Gln Ile Ser Asn Arg Leu Asn Val Gln Ser Arg Gly Leu Asp Val Ala
        50                  55                  60

Val Arg Asn Ala Asn Asp Gly Ile Ser Ile Ala Gln Thr Ala Glu Gly
65                  70                  75                  80

Ala Met Asn Glu Thr Thr Asn Ile Leu Gln Arg Met Arg Asp Leu Ser
            85                  90                  95

Leu Gln Ser Ala Asn Gly Ser Asn Ser Lys Ser Glu Arg Val Ala Ile
            100                 105                 110

Gln Glu Glu Val Thr Ala Leu Asn Asp Glu Leu Asn Arg Ile Ala Glu
            115                 120                 125

Thr Thr Ser Phe Gly Gly Asn Lys Leu Leu Asn Gly Thr Tyr Gly Thr
        130                 135                 140

Lys Ala Met Gln Ile Gly Ala Asp Asn Gly Glu Ala Val Met Leu Ser
145                 150                 155                 160

Leu Lys Asp Met Arg Ser Asp Asn Val Met Met Gly Gly Val Ser Tyr
            165                 170                 175

Gln Ala Glu Glu Gly Lys Asp Lys Asn Trp Asn Val Ala Ala Gly Asp
            180                 185                 190

Asn Asp Leu Thr Ile Ala Leu Thr Asp Ser Phe Gly Asn Glu Gln Glu
            195                 200                 205
```

```
Ile Glu Ile Asn Ala Lys Ala Gly Asp Asp Ile Glu Glu Leu Ala Thr
    210             215                 220

Tyr Ile Asn Gly Gln Thr Asp Leu Val Lys Ala Ser Val Gly Glu Gly
225             230                 235                 240

Gly Lys Leu Gln Ile Phe Ala Gly Asn Asn Lys Val Gln Gly Glu Ile
                245                 250                 255

Ala Phe Ser Gly Ser Leu Ala Gly Glu Leu Gly Leu Gly Glu Gly Lys
            260                 265                 270

Asn Val Thr Val Asp Thr Ile Asp Val Thr Thr Val Gln Gly Ala Gln
        275                 280                 285

Glu Ser Val Ala Ile Val Asp Ala Ala Leu Lys Tyr Val Asp Ser His
    290                 295                 300

Arg Ala Glu Leu Gly Ala Phe Gln Asn Arg Phe Asn His Ala Ile Ser
305             310                 315                 320

Asn Leu Asp Asn Ile Asn Glu Asn Val Asn Ala Ser Lys Ser Arg Ile
                325                 330                 335

Lys Asp Thr Asp Phe Ala Lys Glu Thr Thr Gln Leu Thr Lys Thr Gln
                340                 345                 350

Ile Leu Ser Gln Ala Ser Ser Ser Ile Leu Ala Gln Ala Lys Gln Ala
        355                 360                 365

Pro Asn Ser Ala Leu Ser Leu Leu Gly
    370                 375
```